United States Patent [19]

Eichner et al.

[11] Patent Number: 4,727,018

[45] Date of Patent: Feb. 23, 1988

[54] IMMUNOREGULATION OF TRANSPLANTABLE TISSUE

[76] Inventors: Ronald D. Eichner, 13 Crukshank St., Wanniassa, Australian Capital Territory 2903; Arno Mullbacher, 40 Jennings St., Curtin, Australian Capital Territory, both of Australia

[21] Appl. No.: 733,316

[22] Filed: May 13, 1985

[30] Foreign Application Priority Data

May 18, 1984 [AU] Australia .............................. PG 5053

[51] Int. Cl.⁴ ............................................... A01N 1/02
[52] U.S. Cl. ....................................... 435/1; 435/240; 435/240.1
[58] Field of Search ............................................ 435/1

[56] References Cited

U.S. PATENT DOCUMENTS 3,562,253  2/1971  Trown .
4,117,118  9/1978  Harri et al. .
4,215,199  7/1980  Harri et al. .

FOREIGN PATENT DOCUMENTS 1106303  4/1981  Canada .
0034567  8/1981  European Pat. Off. .

Primary Examiner—Sam Rosen
Attorney, Agent, or Firm—Laubscher & Laubscher

[57] ABSTRACT

Donor tissue is treated prior to implantation in a recipient with a compound from the class known as epipolythiodioxopiperazines in order to prevent graft rejection.

4 Claims, 4 Drawing Figures

IMMUNOREGULATION OF TRANSPLANTABLE TISSUE

BRIEF SUMMARY OF THE INVENTION

This invention relates to clinical transplantation and treatment of autoimmune diseases. The invention is directed to the identification of a class of compounds with antiphagocytic and immunomodulating properties which can prevent graft rejection of donor tissue by a recipient.

BACKGROUND TO THE INVENTION

Immunosuppressive agents are currently employed in a wide variety of medical applications including clinical transplanatation, treatment of autoimmune diseases and investigations into basic immunological functions. In particular, transplantation of organs represents the major solution to human organ failure but immunosuppression of the recipient is essential for graft survival in mismatched donor/recipient combinations.

The current understanding of graft rejection suggests that passenger antigen-presenting cells of donor type are a prerequisite for the induction of the immune response in the recipient which will eventually lead to the rejection of the animal graft. It has been shown that long-term in vitro culture of donor organs (several weeks under high oxygen tension) does selectively deplete such cells and allows successful transplantation.

Unfortunately, most of the drugs commonly used for immunosuppression are themselves toxic and must be administered systemically causing impairment of the host's immune system and other deleterious effects.

Research has established that a fungal product, cyclosporin, can be employed in clinical transplantation with some success. However, nephrotoxicity, hepatotoxicity, systemic adminstration leading to patient susceptibility to opportunistic infection, spontaneous lymphomas, and expensive long-term therapy are among the major drawbacks when using this product. From this earlier research, it is apparent that there still exists a demand for better and less toxic immunomodulating agents.

It is well established (for review see Taylor, A. 1971. The toxicology of sporidesmins and other epipolythiadioxopiperazines. In Microbial Toxins VII, pp 337-376. Edited by S. Kadis, A. Ciegler and S. J. Ajl. New York: Academic Press) that a variety of fungi produce epipolythiodioxopiperazines when cultured in a nutrient broth. These compounds have been investigated in vitro for their potential antibacterial, antifungal, anit-viral and amoebicidal activities. However, their application in vivo has been greatly curtailed by high cellular toxicity in mammals. Indeed, the same has been shown of Trown's (Trown, A. W. 1968. Biochem. Biophys. Res. Commun. 33, 402) synthesized model compound, 1,4-dimethyl-3,6-epidithia-2,5-dioxopiperazine. Accordingly, little is known regarding the effects of any of these fungal or synthesized compounds in vivo.

Experimental allergic encephalomyelitis is an autoimmune demylinating disease of the central nervous system, considered at present the optimal laboratory model for multiple sclerosis. Studies on the pathogenesis of this model disease strongly point to the cellular nature of the immune damage and it is thought that macrophages are important in both afferent and efferent limbs of the immune response leading to the pathological state of experimental allergic encephalomyelitis. Again, nothing is known concerning the effects of these fungal and/or synthesized compounds, belonging to the epipolythiodioxopiperazines, on the etiology of this disease.

One object of the present invention is to provide a method of treating biological material in order to prevent graft rejection in mismatched donor/recipient combinations. By the expression "biological material" is meant any material which may be involved in transplantation procedures such as, for example, single cells, clumps of cells, complete organs, groups of organs or any combination thereof, whether of donor or recipient origin.

A further object of the invention is to provide a method for treating autoimmune diseases.

According to the present invention, a method of treating biological material as defined, comprises subjecting the material with a compound of the general formula (1).

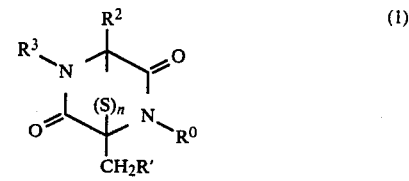

alone or in association with one of more pharmaceutically acceptable carriers or diluents wherein:

$R^0$ and $R^1$ are radicals selected from the group consisting of hydrogen, hydroxy, alkyl, alkoxy and acyloxy; $R^2$ and $R^3$ are radicals separately selected from the group consisting of hydrogen and alkyl; or together, represent a radical of the general formula (2):

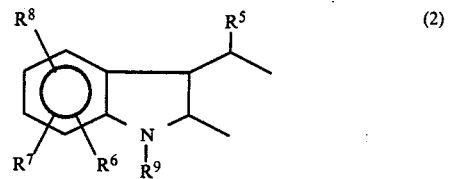

wherein $R^5$, $R^6$, $R^7$, $R^8$ and $R^9$ are radicals separately selected from the group consisting of hydrogen, alkyl, hydroxy, alkoxy, sulfate, and halogen; or $R^2$ and $R^3$ together, represent a radical of the general formula (3):

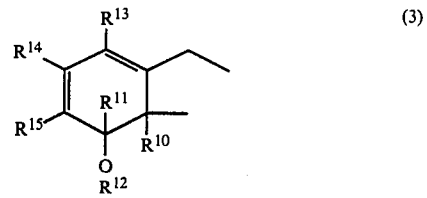

wherein $R^{10}$ and $R^{11}$ both represent hydrogen; or together, represent a valence bond; $R^{12}$, $R^{13}$, $R^{14}$, $R^{15}$ are radicals selected from the group consisting of hydrogen, hydroxy, alkoxy, sulfate and acyloxy; and n is an integer selected from the range 2 to 4.

It has been found that the class of compounds known as epipolythiodioxopiperazines, according to Forumla (1) exhibits anti-phagocytic and immunomodulating properties.

A number of compounds falling within the class of epipolythiodioxopiperazines have been found to be particularly effective in preventing graft rejection, in particular gliotoxin, gliotoxin-tri-sulfide, gliotoxin-tetra-sulfide, sporidesmin, 1,4-dimethyl-3,6-epidithio-2,5-dioxopiperazine and dehydrogliotoxin.

An advantage of the present invention is that it permits the treatment, not necessarily of the recipient, but rather of the donated biological material, for example an organ, in transplantation procedures.

One advantage of treating donated material is that it eliminates the side effects of the currently used immunosuppressive drugs. Specific side effects adverted by the treatments of the present invention include toxicity to organs in the recipient, development of opportunistic infections such as pneumonia, expensive long-term therapy, etc.

It is hypothesised that the treatment of donor material according to the invention results in the selective inactivation of passenger leucocytes within the donor material which are responsible for initiation of graft rejection within the recipient. The treatments according to the invention, unlike conventional treatments, *irreversibly* inactivate the passenger leucocytes, thereby avoiding the need for long-term therapy of the recipient and the resulting deleterious side effects.

It is known that the species of the fungi Aspergillus and Penicillium, and other related fungi, generate metabolites in in vitro cultures that belong the epipolythiodioxopiperazine class of compounds, of which gliotoxin is one, and which can be obtained by modifications of well-published methods (eg. Lowe, G., et al. 1966. J. Chem. Soc., 1799, Dingley et al. 1962. J. Gen Microbiol., 29, 127.).

We have now established that these compounds, display anti-phagocytic activity as tested by macrophage adherence to plastic as well as phagocytosis of particulate matter and, when used to pretreat stimulator spleen cells, inhibit the cells' ability to induce alloreactive and major histocompatibility complex restricted cytotoxic T cells. This is the model system for graft rejection. The metabolites (see FIG. 1) were chloroform-soluble and purified separately into three biologically active compounds on thin-layer chromatography. These compounds were purified (FIG. 2) and one of them was comfirmed as gliotoxin (FIG. 1, n=2). Authentic gliotoxin was found to have similar anti-phagocytic and immunomodulating activity as the purifed sample.

A method for the isolation of substantially pure gliotoxin from fungal cultures is provided by the following examples:

EXAMPLE 1

(a) inoculating agar slopes with *Aspergillus fumigatus*.
(b) suspending conidiospores taken from said agar slopes in Eagle's minimal essential medium F15.
(c) culturing said conidiospores without agitation at 20°–37° C. in a one-half full round bottom flask to ensure sufficient surface area for fungus to grow. Allow fungus to grow for 5–10 days.
(d) separating the fungal mycelium from the culture medium.
(e) sterilising said culture medium by filtration.
(f) extracting said culture medium with an organic solvent such as chloroform.
(g) drying the thus-obtained organic solution and removing said organic solvent by evaporation under vacuum.
(h) isolating gliotoxin from the residue by either preparative thin layer chromatography (on silica and developing in 5% methanol in dichloromethane) or using column chromatography (silica and eluting with a methanol-chloroform gradient, 0–5% methanol); the isolated gliotoxin was then recrystallized from ethanol.

EXAMPLE 2

(a) inoculating agar sloped with *Penicillium terlikowskii* 136 (available through Atlantic Research Laboratories, National Research Council, Canada, Halifax NS) or any of the many available related fungi known to produce gliotoxin in culture (for example, see Taylor, A. 1971. The toxicology of sporidesmins and other epipolythiadioxopiperazines. In Microbial Toxins VII, pp 337–376. Edited by S. Kadis, A. Ciegler and S. J. Ajl. New York: Academic Press).
(b) the subsequent steps are quite similar though it will be appreciated that the nutrient broth, temperature at which the fungi are grown and the duration can all vary according to the requirement of the fungi.

It was also found that *A. fumigatus* generated two additional and previously unknown metabolites in in vitro cultures which displayed anti-phagocytic activity as tested by macrophage adherence to plastic. The metabolites appeared at 3 days of culture and reached a peak concentration at days 5–7 (FIG. 4). The metabolites were chloroform soluble and were separated and purified on thin layer chromatography (FIG. 2). They were identified as gliotoxin trisulfide (FIG. 1; n=3) and gliotoxin tetrasulfide (FIG. 1; n=4).

Thus according to a further aspect of the present invention, there is provided a method for the isolation of substantially pure gliotoxin tri- and tetrasulfide from *A. fumigatus*, said method comprising:

EXAMPLE 3

(a) inoculating agar slopes with *Aspergillus fumigatus*.
(b) suspending conidiospores taken from said agar slopes in Eagle's minimal essential medium F15.
(c) culturing said conidiospores without agitation at 20°–37° C. in a one-half full round bottom flask to ensure sufficient surface area for fungus to grow. Allow fungus to grow for 5–10 days.
(d) separating the fungal mycelium from the culture medium.
(e) sterilising said culture medium by filtration.
(f) extracting said culture medium with an organic solvent such as chloroform.
(g) drying the thus-obtained organic solution and removing said organic solvent by evaporation under vacuum.
(h) isolating gliotoxin tri- or tetrasulfide from the residue by either preparative thin layer chromatography (on silica and developing in 5% methanol in dichloromethane) or using column chromatography (silica and eluting with a methanol-chloroform gradient, 0–5% methanol); the isolated gliotoxin tri- and tetrasulfides then recrystallized from ethanol.

EXAMPLE 4

(a) inoculating agar slopes with *Penicillium terlikowskii* 136 (available through Atlantic Research Laboratories, National Research Council, Canada, Halifax NS)

or any of the many available related fungi known to produce gliotoxin in culture (for example, see Taylor, A. 1971. The toxicology of sporidesmins and other epipolythiadioxopiperazines. In Microbial Toxins VII, pp 337–376. Edited by S. Kadis, A. Ciegler and S. J. Ajl. New York: Academic Press).

(b) the subsequent steps are quite similar though it will be appreciated that the nutrient broth, temperature at which the fungi are grown and the duration can all vary according to the requirement of the fungi.

It has now been discovered that gliotoxin, gliotoxin-trisulfide and gliotoxin-tetrasulfide and related compounds belonging to the class of epipolythiodioxopiperazines inhibit phagocytosis by macrophages (Table 1), white cells that participate in the host's defense system against infection and co-operate with other immune cells in mounting an immune response. One aspect of this defense system, which is shared by all stimulator cells (macrophage-like white cells), is the presentation of antigen by the cells of one animal to responder lymphocytes (another white cell) of another animal with the subsequent generation of cytotoxic or killer T cells. This model, that is, in vitro induction of alloreactive cytotoxic T cells, represents a model for graft rejection which in turn is the major obstacle to transplantation of organs. It has been discovered that this induction of alloreactive cytotoxic T cells is abrogated by gliotoxin and other compounds belonging to the epipolythiodioxopiperazines (Tables 2, 3). Further, other immune functions are also irreversibly inhibited by these compounds (Tables 4, 5).

Thus, according to another aspect of the present invention, there is provided a class of compounds, structurally related to gliotoxin and substantially pure, which exhibit similar anti-phagocytic and immunomodulating properties to those of gliotoxin, said compounds having the general formula (1).

A still further aspect of the present invention is a method of modulating or suppressing the immune response of animals (including humans) by the administration of one or more compounds of the general formula (1).

Another aspect of the present invention is the provision of a method of treating animal (including human) tissue or donor animals in situ for transplantation to a recipient, said method comprising incubating said tissue in the presence of one or more compounds of the general formula (1) prior to implantation of said tissue into said recipient; or administering one or more compounds of the general formula (1) to donor animals prior to implantation of said tissue into recipient animals.

A further aspect of the present invention is the provision of a method of preventing the onset of experimental allergic encephalomyelitis by treatment of sensitized donor immune cells with compounds of the general formula (1) prior to implantation into recipient animals.

Details of the materials and methods as used in the present invention will now be described. In this description, all temperatures are in degrees centigrade, and technical terms and abbreviations have the usual meaning in the art. Crude reagents, products and preparations can be purified by the means described herein, or by other means known in the art.

DETAILED DESCRIPTION OF EMBODIMENTS

Figure 1:
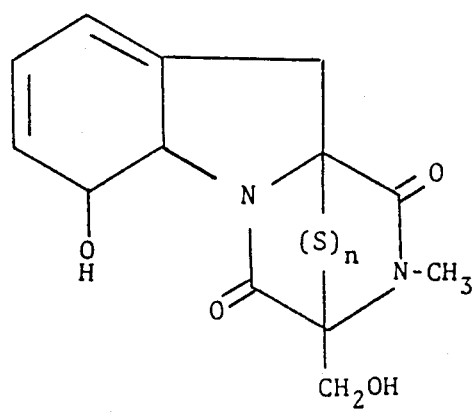

Test Animals:
CBA/H, BALB/c and C57BL/10 mice and DA rats of either sex were used at 6–12 weeks of age.

Preparation of Culture Supernatants of *Aspergillus Fumigatus* (SAF):

Conidiospores, taken from agar slopes previously inoculated with *A. fumigatus* were suspended in Eagles minimal essential medium F15 (Grand Island Biological Co., Grand Island, NY) and cultured without agitation for 5–7 days at 24° or 37°. The fungal mycellium was separated by passing the culture medium through a nylon mesh, and then sterilized by filtration (Millex-GS, 0.22 um, Millipore SA, Molsheim, France).

Preparation of Culture Supernatants of *Penicillium Terlikowskii*:

Condiospores, taken from agar slopes previously inoculated with *P. terlikowskii* were suspended in Weindling medium (consisting of 25 g glucose, 2 g ammonium tartrate, 100 mg $KH_2PO_4$, 500 mg $MgSO_4$, 100 mg yeast extract, 1 mg $FeSO_4xH_2O$, 0.15 mg $CuSO_4xH_2O$, 1 mg $ZnSO_4xH_2O$, 0.15 mg $MnSO_4xH_2O$ and 0.15 mg $K_2MoO_4$) and cultured without agitation for 10–25 days at 20°–24°. The fungal mycellium was separated by passing the culture medium through a nylon mesh, and then sterilized by filtration.

Source of Other Epipolythiodioxopiperazines:

The naturally occurring members of the epipolythiodioxopiperazines used in the subsequent studies outlined below were either obtained as described in the literature, or, for gliotoxin, gliotoxin-tri-sulfide and gliotoxin-tetra-sulfide, prepared according to the details as outlined below. Authentic samples of gliotoxin, dehydrogliotoxin and sporidesmin were kindly provided by one or both of the following sources: R. Gallagher, Ruakura Animal Research Station, Hamilton, New Zealand and A. Taylor, Atlantic Research Laboratory, Halifax, Nova Scotia, Canada. The 1,4-dimethyl-3,6-epidithio-2,5-dioxopiperazine was prepared according to Trown (Trown, A. W. 1968. Biochem, Biophys. Res. Commun. 33, 402). All epipolythiodioxopiperazines were dissovled in absolute ethanol at 1 mg/ml and stored in aliquots at −70° until needed.

CELL LINES

Thioglycollate-induced peritoneal macrophages (TGM) were harvested from thioglycollate-injected mice [intraperitoneal (i.p.) injection of 2 ml of 3% (w/v) thioglycollate (Difco Labs, Detroit, MI) solution 5–8 days previously] by the i.p. injection of 7 ml of ice-cold Puck's saline and withdrawal of the saline with a syringe and 20-gauge needle, and consisted of greater than 83% macrophages and monocytes as determined by staining (Diff Quick Set, AHS/Australia) of cytocentrifuge smears. TGM were then pelleted by centrifugation and resuspended in F15 plus 5% foetal calf serum (FCS).

Concanavalin A (Con A)—activated lymphocytes, BW5147 and P815 tumor cells were grown and labeled with neutral red or with $^{51}Cr$ as described by Mullbacher A., Parish C. R., Mundy J. P. (1984), *J. Immunol. Methods*, 68, 205–215.

The tumor cell line L929, BW 5147, R1+, EL4 and P815 and secondary mouse embryo fibroblasts (FB) were grown in Dulbecco's modified Eagle's medium H16 (Grand Island Biological Co., Grand Island, N.Y.) containing 5–6% FCS.

Rat polymorphonuclear cells were also obtained from thioglycollate-treated animals and freed from adherent cells as described by Eichner R. D. & Smeaton T. C., *Scand. J. Immunol.*, 18, 259–263 (1983).

Resident and influenza-elicited (500 HAU of A/WSN influenza administered intranasally) alveolar macrophages were obtained from rats by repeated lung lavages with PBS.

PREPARATION OF CON A-ACTIVATED CELL SUPERNATANTS

The preparation and assay of Con A-activated cell supernatants followed the procedures described by Lafferty K. J. et al, (1980) *Aust. J. Exp. Biol. Med. Sci.*, 58, 533-544.

MIXED LYMPHOCYTE CULTURES (MLCs)

Resonder spleen cell suspension ($2 \times 10^6$ cells per ml) were cocultured for 5 days at 37° C. in humidified 5% $CO_2$/95% air with either $2 \times 10^6$ allogeneic spleen cells (inactivated by 2000 R from a $^{60}Co$ source) or $1 \times 10^6$ allogeneic TGM in a 5 ml of Eagle's minimal essential medium F15 containing 5% foetal calf serum and $10^{-4}M$ 2-mercaptoethanol.

CYTOTOXICITY ASSAY AND ANTIBODY AND COMPLEMENT-MEDIATED LYSIS

The $^{51}Cr$ release assay for cytotoxic cells using P815, L929, BW5147, Con A blasts and TGM and lysis followed the procedures described by Mullbacher A., Parish C. R. & Mundy J. P., (1984), *J. Immunol. Methods*, 68, 205-215.

NEUTRAL RED CELL ADHERENCE ASSAY

The method used is that described by Mullbacher A., and Eichner R. D., (1984), *Proceedings of the National Academy of Sciences (U.S.A.)*, 81, 38935-3837. In brief, $5 \times 10^6 - 5 \times 10^7$ TGM, L929 or FB were labelled in suspension for 15 min at 37° C. in 5 ml of 0.04% (w/v) neutral red (NR) (Cl 50040, BDH) in Hank's balanced salt solution. The cells were pelleted, washed twice in F15 containing 1% FCS and resuspended at $5 \times 10^5$ cells $ml^{-1}$. Aliquots (0.1 ml) were distributed in each well of a 96-well round-bottom tissue culture plate (cat. no. 75-013-05; Linbro Division, Flow Laboratories, Hamden, CT). The plates initially contained 0.1 ml aliquots of solutions containing compounds belonging to the epipolythiodioxopiperazines or dilutions thereof prior to the addition of NR-labelled cells. After an appropriate incubation at 37° C., the medium was thrown off and cell monolayers washed by immersing the microplate once in a phosphate-buffered saline (PBS) (0.143M sodium chloride, 0.01M sodium phosphate, pH 7.4) bath. The PBS was thrown off and the NR was released from the remaining adherent cells by addition of 0.1 ml/well of 0.05M acetic acid in 50% ethanol whereupon optical density at 540 nm was measured by a microplate reader (Dynatech 500 or ELISA).

GENERATION AND CYTOTOXICITY TESTING OF ALLOREACTIVE AND MHC-RESTRICTED CYTOTOXIC T CELLS

The methods used are those described by (Mullbacher et al., 1984), *Journal of Immunological Methods*, 68, 205-215. In summary, female C57BL/10 mice were immunised with $10^7$ syngeneic male spleen cells i.p. and used after a minimum of four weeks post-priming. For the generation of alloreactive and major histocompatibility complex (MHC) restricted cytotoxic T cells, $10^7$ spleen responder cells from previously immunised animals were cocultured with $4 \times 10^6$ CBA/H or $5 \times 10^6$ male C57BL/10 irradiated (2000 R from a $^{60}Co$ source) spleen stimulator cells respectively. The cells were incubated in 5 ml F15 containing 5% FCS plus $10^{-4}M$ 2-mercaptoethanol in 12-well culture dishes (Costar, Cambridge, Mass.) for 5 days at 37° C. in a humidified 5% $CO_2$ atmosphere.

The cultures were harvested and 0.1 aliquots of cells titrated in three-fold dilution steps into 96-well round-bottom tissue culture plates. TGM target cells were labelled with $^{51}Cr$ (Amersham, England) for 1 hr, washed thoroughly and added in 0.1 ml aliquots at $2 \times 10^5$ cells/ml and incubated at 37+ C. for 6 hr. 0.1 ml of individual well supernatants were removed and radioactivity measured in a gamma-counter. Medium release was estimated by culturing target cells in the absence of effector cells. Total releasable $^{51}Cr$ was estimated by lysing target cells with 1% Triton-X solution. Percent specific lysis was calculated by the formula:

$$\text{percent specific lysis} = \frac{\text{experimental release} - \text{medium release}}{\text{maximum release} - \text{medium release}} \times 100\%$$

SPECTROSCOPIC STUDIES OF PURIFIED METABOLITES

Proton nuclear magnetic resonance spectroscopy (NMR) was performed on a JEOL FX90Q spectrometer operating at 89.56 $MH_z$ at 37°. Checmical shifts were measured downfield in ppm from added trimethylsilane (TMS). Infra-red spectra (IR) were run in KBr on a Unicam SP1000 spectrometer. Mass spectra (MS) were run on an MS-9 spectrometer.

CALCULATION OF BIOLOGICAL ACTIVITY

The absorbance at 540 nm, indicative of the residual adherent neutral red-labelled TGM population, was plotted against the dilution of solutions containing epipolythiodioxopiperazines. Similar plots were constructed as a function of concentration for known or identified substances. The effective dilution of unknown samples is defined as that dilution which results in 50% of the maximum observed loss of adherent TGM; the corresponding parameter for purified fractions of known compounds is expressed as the $ED_{50}$ or effective dose. The amount of biological activity in culture or purified fractions is determined by the following formula:

$$\text{activity} = \frac{ED_{50} \text{ or effective dilution}}{ED_{50} \text{ for authentic gliotoxin}} \times (\text{gliotoxin})_{Std}$$

where $(\text{gliotoxin})_{Std}$ refers to the concentration of an authentic gliotoxin solution (usually 1-10 ug/ml). An additional dilution factor was applied when analysing concentrated chloroform extracts.

PHAGOCYTOISIS OF PARTICULATE MATTER

Cells ($5 \times 10^6$/ml) in Eagle's minimal essential medium F15 (Grand Island Biological Co., Grand Island, N.Y.) supplemented with 5% FCS were preincubated for 30 min at 37° C. in the absence or presence of GT (1-1000 ng/ml). Phagocytosis of various particules was then initiated for a further 30-180 min whereupon the assays were initially quenched by cooling to 4° C. Specifically, carbon (Pelican India Ink, West Germany) uptake was measured by the method described by Jaffe P., and Yoffey J. M., *J. Anat.*, 134, 729-740 (1982).

Quantitation involved measurement of turbidity at 800 nm of cells lysed (50 mM acetic acid, 50% ethanol) after removal of non-phagocytosed material by centrifugation of the cells and/or the estimation by light microscopy by counting 200 mononuclear cells. The phagocytosis of carbon expressed as the percent of control is defined either as (1) the number of cells containing carbon in the treated samples divided by that number in the control sample, or (2) the turbidity at 800 nm of the treated cells divided by that of the control cells.

Phagocytosis of carbonyl iron was measured by light microscopy following the method described by Koren H. S., and Hodes R. F., *Eur. J. Immunol.*, 7, 394–400 (1977).

Uptake of fluorescent microspheres (0.57 um diameter; Polysciences Inc., Warrington, PA) was analyzed by the fluorescent-activated cell sorter. A plot of fluorescence intensity as a function of particule number (200,000 events per sample) was obtained and then integrated (Planix 7, Tamaya & Co., Tokyo).

The inhibitory effects of GT upon phagocytosis is generally expressed in terms of the $ED_{50}$ value which is defined as that concentration of GT which resulted in one-half the measured inhibitory effect.

Details of the results obtained from the present invention will now be described.

Purification of *A. Fumigatus* Metabolites:

The biologically active components from *A. fumigatus* culture supernatants were purified over 1000-fold by chloroform extraction, thin layer chromatography and recrystallization (Table 6). Other components isolated from said supernatants were ineffective in the TGM adherence assay.

Purification of *P. terlikowskii* Metabolites:

Virtually identical procedures were employed to isolate and purify the active metabolites in culture supernatants of said fungus.

Identification of Gliotoxin, Gliotoxin-tri-sulfide and Gliotoxin-tetra-sulfide in Culture Supernatants of *A. Fumigatus:*

Figure 2:
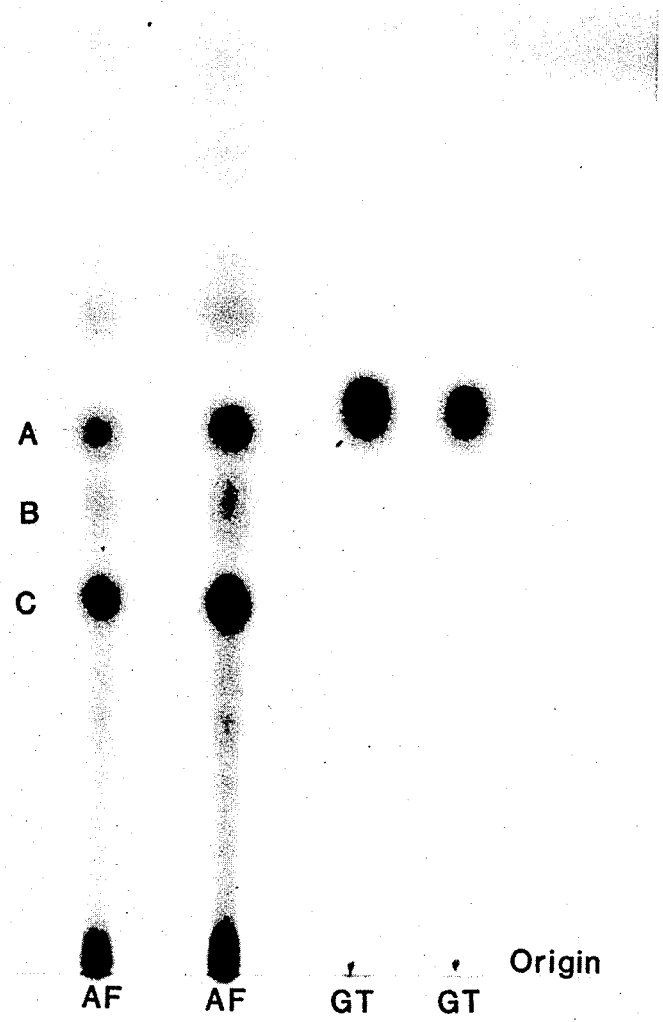

Premilinary studies indicated that the active components (A, B, C, in FIG. 2) present in these supernatants had the following properties:
(1) molecular weight less than 500 as determined by gel filtration;
(2) stable to digestion with trypsin, protease and glycosidases; and
(3) unstable to heating in weak alkali with the concomitant release of sulphide as measured by the lead acetate test.

Figure 3:
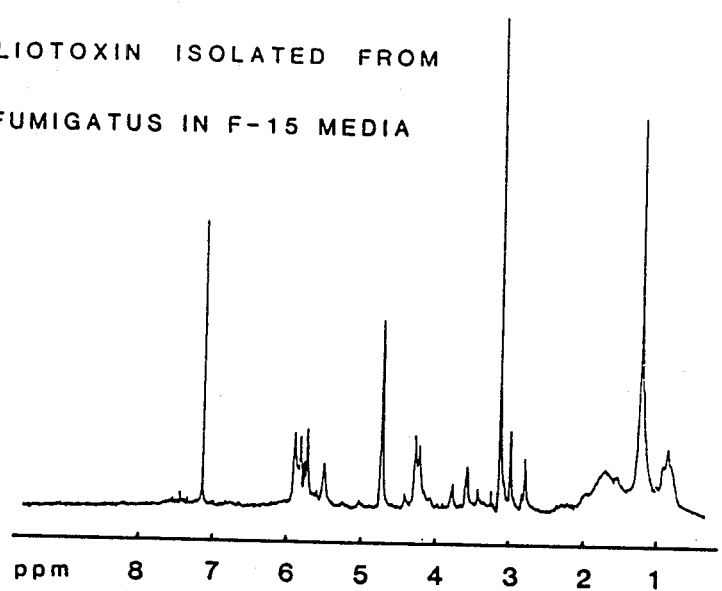
Figure 3:
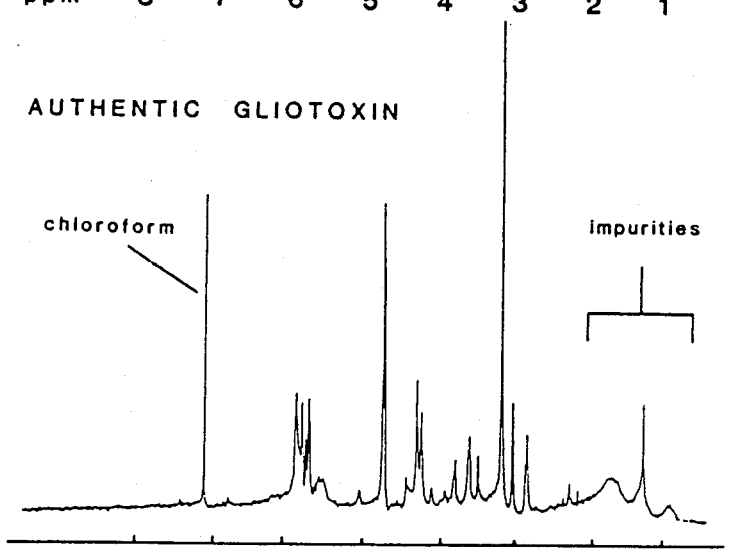
Figure 4:
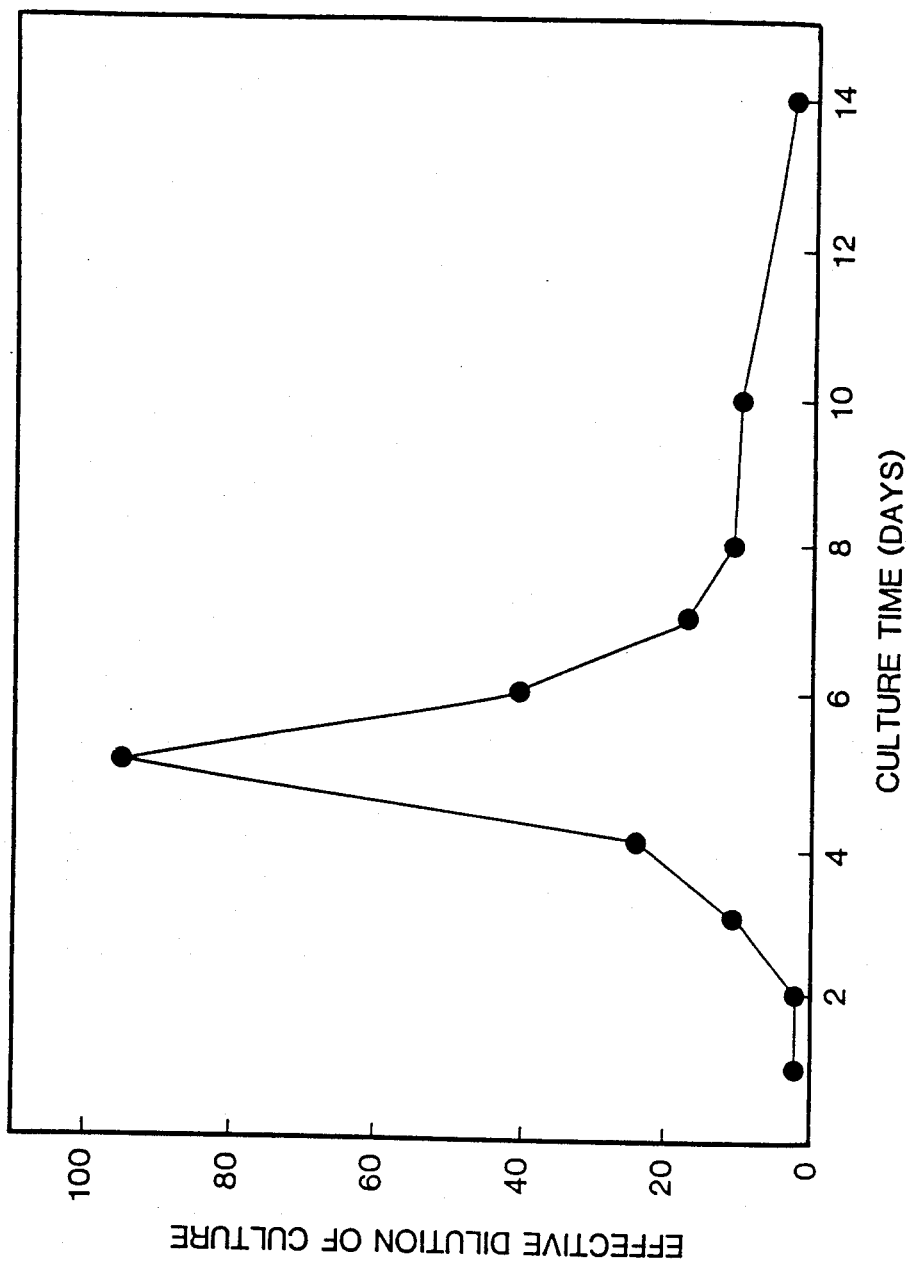

The $R_f$ values for the biologically active components were 0.49, 0.41 and 0.34 for Component A, B and C respectively. The $R_f$ value for purified authentic gliotoxin was 0.50. FIG. 3 illustrates the NMR spectrum for both authentic gliotoxin (lower panel) and that for the component with an $R_f$ value of 0.49 (upper panel). The following frequencies in $cm^{-1}$ represent the peaks observed in the IR of said component: 3450(m), 2930(w), 1670(s), 1460(w), 1380(w), 1280(w), 1240(w), 1200(w), 1060(w), 720(2), 660(w) and 640(w) where s, m, and w refer to strong, medium or weak absorbances. A sample of authentic gliotoxin had an identical IR spectrum.

TABLE 6

Purification of biologically active components of

| Step | Activity[a] (mg/l) | Recovery (%) | Specific activity[b] | Fold purification |
|---|---|---|---|---|
| SAF | 12.0 | 100 | 0.0007 | 1 |
| Chloroform extraction | 10.6 | 88 | 0.16 | 230 |
| TLC | 7.4 | 62 | 0.76 | 1100 |
| Recrystallization[c] | | | | |
| Component A | 2.1 | | $0.95 \pm 21\%$[d] | |
| Component B | 1.6 | | $1.2 \pm 29\%$ | |
| Component C | 3.7 | | $0.6 \pm 22\%$ | |

[a]Expressed as the ratio of the effective dilution or $ED_{50}$ value in the TGM adherence assay relative to that value for authentic gliotoxin: the ratio was then multiplied by the concentration of the non-diluted gliotoxin standard solution.
[b]Activity divided by the weight of non-volatile components.
[c]Individual biologically active components wherein A, B, C, refer to gliotoxin, gliotoxin-tri-sulfide and gliotoxin-tetra-sulfide, respectively that were removed from TLC plates and recrystallized from either ethanol or.
[d]The specific activity ± coefficient of variation as compared to authentic gliotoxin.

Electron impact mass spectroscopy of Component A gave $M^+$ at 262, 244, 226, and 214. No fragments with m/e greater than 262 were observed. Chemical ionization of Component A gave $M^+ +1$ at 327, 263 ($M^+ +1-S_2$), 245($M^+ +1-S_2-H_2O$) and 227 ($M^+ +1-S_2-2H_2O$). Chemical ionization of Component C gave $M^+ +1$ at 391, 359 ($M^+ +1-S$), 327 ($M^+ +1-S_2$), 263 ($M^+ +1-S_4$), 245 ($M^+ +1-S_4-H_2O$) and 227 ($M^+ +1-S_4-2H_2O$).

The high resolution chemical ionization mass spectra indicated the following: $M^+ +1$ at 327.0472, best fit formula=$C_{13}H_{14}N_2O_4S_2$ (expected=327.0473) for Component A; 359.0193, best fit formula=$C_{13}H_{14}N_2O_4S_3$ (expected=359.0194) for Component B; 390.9914, best fit formula=$C_{13}H_{14}N_2O_4S_4$ (expected=390.9915) for Component C. The high resolution NMR data for Components B and C combined with the fragmentation pattern in the mass spectra verifies a gliotoxin-like structure.

The optical rotation of Component C ($CHCl_3$, conc.=$2.33 \times 10^{-4}M$) was $(M)_{404}-1890°$, $(M)_{435}-1500°$, $(M)_{500}-970°$, $(M)_{577}-620°$. The literature value for authentic gliotoxin is $(M)_{589}-890°$ ($CHCl_3$, conc.=0.103M). The corresponding values for authentic gliotoxin in out hands were $(M)_{404}-1480°$, $(M)_{435}-1220°$, $(M)_{500}-864°$, $(M)_{577}-593°$ ($CHCl_3$, conc. $1.18 \times 10^{-3}M$). Thus the ORD curve for Component C, or gliotoxin-tetrasulfide, between 400 and 577 nm is identical to that of authentic gliotoxin except for an enhancement of 13–30%, indicating the same absolute configuration of the disulfide moiety.

The chemical properties, stability characteristics, TLC mobility, high resolution NMR, IR and mass spectroscopy combined with comparisons of authentic samples of gliotoxin permit identification of Components A, B, C as gliotoxin, gliotoxin-tri-sulfide and gliotoxin-tetra-sulfide, respectively. Indeed in the high resolution mass spectra of Components A, B, C, the fragmentation patterns are identical except for the initial additional losses of sulfur for Components B and C.

Effects of Epipolythiodioxopiperazines on Phagocytosis:

These effects are contained in Table 1. The uptake of carbon by TGM was inhibited 82% with gliotoxin (1000 ng/ml). The concentration of gliotoxin which resulted in one-half the observed effect ($ED_{50}$ in ng/ml) was similar for all particles and for both elicited and resident cell populations.

Adherence to plastic surfaces, which is akin to phagocytosis for macrophages and monocytes was inhibited by gliotoxin in a dose dependent manner as reflected in the values for $ED_{50}$ (Table 1). Table 7 illustrates the effects of a variety of epipolythiodioxopiperazines on phagocytosis by macrophages. All of these compounds inhibit phagocytosis. Table 8 demonstrates that other fungal metabolites which do not possess the epipolythiodioxopiperazine moiety have no activity. The fact that the dimethythioether derivative of gliotoxin also has no activity in this assay emphasizes the essentiality of the epipolythiodioxopiperazine moiety of these compounds.

TABLE 1

Effect of gliotoxin on phagocytosis and related processes

| Substrate | Cell | $ED_{50}$[a] ng/ml | Inhibition[b] % |
|---|---|---|---|
| Carbon | Rat TG-MØ | 100 ± 14 | 82 ± 7 |
|  | Rat resident MØ | 95 ± 15 | 73 ± 10 |
| Carbonyl iron | Rat TG-MØ | 88 ± 10 | 54 ± 7 |
| Fluorescent latex beads | Rat TG-MØ | 105 ± 5 | 86 ± 14 |
| Adherence to Plastic | Rat TG-MØ | 76 ± 17 | ≧95 |
|  | Rat resident MØ | 82 ± 13 | ≧95 |
|  | Rat alveolar MØ | 37 ± 10 | ≧95 |
|  | Rat influenza-alveolar MØ | 49 ± 8 | ≧95 |
|  | Mouse TG-MØ | 34 ± 5 | ≧95 |
|  | Human peripheral blood monocytes | 19 ± 1 | ≧95 |
|  | Mouse secondary fibroblasts | 168 ± 18 | ≧95 |
|  | L929 cells | 311 ± 35 | ≧95 |

[a]Values represent the mean ± standard error for at least three determinations.
[b]Defined at 1000 ng/ml gliotoxin as compared to control.

TABLE 7

Effect of Epipolythiodioxopiperazines on TGM Phagocytosis

| Compound | $ED_{50}$[a] |
|---|---|
| Gliotoxin | 34 |
| Gliotoxin-tri-sulfide | 30 |
| Gliotoxin-tetra-sulfide | 56 |
| Sporidesmin | 4 |
| 1,4-dimethyl-3,6-epidithio-2,5-dioxopiperazine | 67 |
| Dehydrogliotoxin | 39 |
| S,S—dimethylthioether derivative of gliotoxin[b] | ≧5000 |

[a]$ED_{50}$ values in ng/ml in the macrophage adherence assay.
[b]Represents the only compound in this series which does not possess the intact disulfide portion of the epipolythiodioxopiperazines.

TABLE 8

The effect of fungal metabolites upon macrophage adherence

| Compound | $ED_{50}$[a] |
|---|---|
| Gliotoxin | 44 ng/ml |
| Helvolic acid | ≧1.3 mg/ml |
| Cytochalasin B | ≧5 mg/ml |
| Fumagillin | ≧0.5 mg/ml |
| Penicillin | ≧0.5 mg/ml |
| Streptomycin | ≧0.5 mg/ml |

[a]$ED_{50}$ refers to the concentration of compound required to inhibit TGM adherence by 50%.

Effects of epipolythiodioxopiperazines on immune function:

Unless otherwise indicated all values mentioned herein are subject to the usual experimental errors, i.e. those skilled in the art will appreciate that modifications and variations to the invention described above and below are possible without departing from the present invention concept.

(1) The effect of epipolythiodioxopiperazines on inhibition of BALB/c anti C57BL/10 alloreactive cytotoxic T cell generation in vitro is as below:

TABLE 2

| Stimulator Cell | Compound | $ED_{50}$ |
|---|---|---|
| Spleen | Gliotoxin | 100 ng/ml |
| TGM | Gliotoxin | 30 ng/ml |
| Spleen | Sporidesmin | 10 ng/ml |
| TGM | Sporidesmin | 4 ng/ml |

(2) The effect of gliotoxin on the induction of CBA anti BALB/c alloreactive cytotoxic T cells in vitro is as below:

TABLE 3

| Treatment of Stimulator Cells | % Specific lysis of $^{51}$Cr-P815 |
|---|---|
| None | 55.3 (1.3) |
| Gliotoxin (1000 ng/ml) | −0.4 (0.3) |
| Gliotoxin (100 ng/ml) | 4.1 (0.4) |
| Gliotoxin (1000 ng/ml) and CS | 0.1 (0.5) |
| Gliotoxin (100 ng/ml) and CS | 58.8 (1.5) |
| UV irradiation | 3.3 (0.6) |
| UV irradiation and CS | 60.5 (4.1) |

CS, ConA-activated lymphocyte supernatant. @Mean percent specific $^{51}$Cr release over a 4-hr period. Spontaneous release was 16%. The values from titration curves 1/30 fraction of culture. SEM of three replicate is given in parentheses.

(3) The effect of gliotoxin on target cell lysis in cytotoxic T cell assays in vitro is as below:

TABLE 4

| $ED_{50}$ | TGM | L929 | BW | Con A blast |
|---|---|---|---|---|
| Gliotoxin | 30 | 1000 | 800 | 1000 |

*$ED_{50}$ values are in ng/ml and represent that concentration of gliotoxin which inhibited target cell lysis by 50%.

(4) The effect of epipolythiodioxopiperazines on T and B lymphocyte proliferation in response to mitogens in vitro as below:

TABLE 5

| Compound | $ED_{50}$* |
|---|---|
| Gliotoxin | 15 |
| Sporidesmin | 2 |
| Dehydrogliotoxin | 25 |
| 1,4-dimethyl-3,6-epidithio-2,5-dioxopiperazine | 150 |

*$ED_{50}$ values are in ng/ml and represent that concentration of these compounds which inhibited T and B lymphocyte proliferative responses to the mitogens LPS and Con A.

Epipolythiodioxopiperazines are useful by their effects on humoral and cellular immunity as indicated in the above standard tests. Thus, they are useful in the suppression or formation of or proliferation of immunocytes or lymphocytes and are therefore useful in the treatment of autoimmune diseases, and suppressing the rejection of transplants e.g. thyroid, skin and pancreatic islet cells. Details are as below.

Use of Gliotoxin in prevention of graft rejection:
(1) Thyroids:
Thyroids from donor animal (mice) were removed under anesthesia and transferred to sterile media (F15) containing gliotoxin (0–1000 ng/ml). Thyroids were then incubated at 37° in a humidified $CO_2$ incubator (5% $CO_2$ in air) for 6–18 hours. The tissues were then washed with fresh F15 or equivalent and then implanted under the kidney capsule of the recipient allogeneic mouse. Graft function was evaluated histologically and functionally, the latter by actual uptake of radioactive iodine. In these experiments, none out of 20 allografts which received no gliotoxin was accepted by recipient mice. However 9 out of 30 treated grafts were successful. In these experiments recipient animals received no treatment (i.e. immunosuppression) other than anesthesia for surgery.

(2) Skin:

Initial studies with mouse tail skin indicates that pretreatment of donor skin will permit prolongation of the period of survival in major histocompatibility complex incompatible mice as compared to untreated tissues. Specifically, in vitro culturing or donor tissues in a suitable medium such as F15 in the presence of gliotoxin (1000 ng/ml) prolonged graft survival by 7–15 days.

(3) Pancreatic Islets:

In vitro culturing of pancreatic islets from donor mice in the presence of gliotoxin (1000 ng/ml, 37° for 12–18 hours) permitted successful grafts in 5 out of 5 animals of a different strain, i.e. allogeneic transfer. The methods of preparation of and transplanting pancreatic islets is well documented. These grafts have been in place for more than 3½ months. None of the 5 control allogeneic transplants performed in the absence of gliotoxin were successful. Morphological and functional studies confirmed these results. Specifically, islets from four fetal donors were treated with gliotoxin as above and then transplanted under the kidney capsule of one recipient allogeneic recipient made diabetic with streptozotocin. Euglycemia after 4-6 weeks was achieved in this animal. All ten isografts treated as above with gliotoxin were successfully transplanted without any signs of rejection.

Use of epipolythiodioxopiperazines in experimental allergic encephalomyelitis:

The apparent cellular nature of the immune damage in this disease and the macrophage component thereof provides for a good model for effects of said compounds on macrophage function in vivo. Induction of this disease involves passive immunisation whereby spleen cells from animals previously immunised with myelin basic protein are then transferred to naive animals. Preincubation of these spleen cells with either gliotoxin (100–1000 ng/ml) sporidesmin (3–300 ng/ml) or 1,4-dimethyl-3,6-epidithio-2,-5-dioxopiperazine (300–1000 ng/ml) completely prevented disease (as measured by neurological signs and pathological examination of the central nervous system) in 5 out of 5 for each of the treatments. Nine out of 10 controls that had no pretreatment of spleen cells with these compounds were paralysed.

For all the above uses, the dosages will of course vary depending on the compound employed, mode of administration and treatment desired.

What is claimed is:

1. A method of treating transplantable biological material to produce anti-phagocytic and immunomodulating properties comprising contacting said material with an effective amount of a compound of the general formula (1):

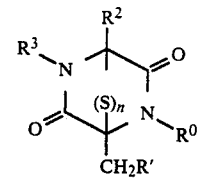

alone or in association with one or more pharmaceutically acceptable carriers or diluents wherein $R^0$ and $R^1$ are radicals selected from the group consisting of hydrogen, hydroxy, alkyl, alkoxy and acyloxy; $R^2$ and $R^3$ are radicals separately selected from the group consisting of hydrogen and alkyl; or together, represent a radical of the general formula (2):

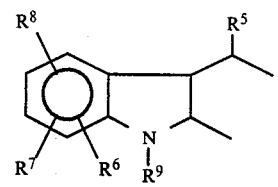

wherein $R^5$, $R^6$, $R^7$, $R^8$ and $R^9$ are radicals separately selected from the group consisting of hydrogen, alkyl, hydroxy, alkoxy, sulfate, and halogen; or $R^2$ and $R^3$ together, represent a radical of the general formula (3):

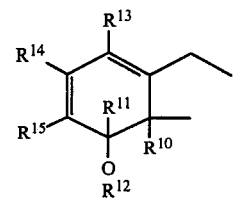

2. A method of treating biological material for transplantation to a recipient, said method comprising incubating said material prior to transplantation, alone or in association with one or more pharmaceutically acceptable carrier or diluents, with an effective amount of a compound of the general formula (1).

3. A method according to claim 2, said method comprising incubating said material prior to transplantation in the presence of a compound selected from the group consisting of gliotoxin, gliotoxin-tri-sulfide, gliotoxin-tetra-sulfide, sporidesmin, 1,4-dimethyl-3,6-epidithio-2,5-dioxopiperazine and dehydrogliotoxin, or derivatives thereof as described in general formulas 2 and 3.

4. A method according to claim 1, comprising incubating said material in the presence of a compound selected from the group consisting of gliotoxin, gliotoxin-tri-sulfide, gliotoxin-tetra-sulfide, sporidesmin, 1,4-dimethyl-3, 6-epidithio-2, 5-dioxopiperazine and dehydrogliotoxin, or derivatives thereof as described in general formulas 2 and 3.

* * * * *

UNITED STATES PATENT AND TRADEMARK OFFICE
CERTIFICATE OF CORRECTION

PATENT NO. : 4,727,018
DATED : February 23, 1988
INVENTOR(S) : Eichner, Ronald D. et al It is certified that error appears in the above—identified patent and that said Letters Patent is hereby corrected as shown below:

In the Heading:

Indicate the Assignee to be:

-- The Australian National University,
   Acton, the Australian Capitol Territory,
   Commonwealth of Australia --

Signed and Sealed this

Sixteenth Day of August, 1988

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,727,018

DATED : February 23, 1988

INVENTOR(S) : EICHNER, Ronald D. et al

It is certified that error appears in the above—identified patent and that said Letters Patent is hereby corrected as shown below:

In claim 1, after formula (3), insert:

-- wherein $R^{10}$ and $R^{11}$ both represent hydrogen; or together, represent a valence bond; $R^{12}$, $R^{13}$, $R^{14}$, $R^{15}$ are radicals selected from the group consisting of hydrogen, hydroxy, alkoxy, sulfate and acyloxy; and n is an integer selected from the range 2 to 4 --

Signed and Sealed this

Twenty-fifth Day of April, 1989

Attest:

DONALD J. QUIGG

*Attesting Officer*　　　*Commissioner of Patents and Trademarks*